United States Patent [19]

Kluender

[11] 4,100,356
[45] Jul. 11, 1978

[54] DEPENTYL ANALOGUES OF PGE₁

[75] Inventor: Harold Clinton Kluender, Madison, Wis.

[73] Assignee: Miles Laboratories, Inc., Elkhart, Ind.

[21] Appl. No.: 787,480

[22] Filed: Apr. 14, 1977

Related U.S. Application Data

[62] Division of Ser. No. 684,569, Feb. 9, 1977, Pat. No. 4,065,493.

[51] Int. Cl.² .............................................. C07C 177/00
[52] U.S. Cl. ................................. 560/121; 260/514 D
[58] Field of Search .................... 260/514 D; 560/121

[56] References Cited

FOREIGN PATENT DOCUMENTS 2,515,703 10/1975 Fed. Rep. of Germany ....... 260/468

Primary Examiner—Robert Gerstl
Attorney, Agent, or Firm—Myron B. Sokolowski

[57] ABSTRACT

Depentyl analogues of prostaglandins A, E, and F having no C-16 to C-20 carbon atoms. The analogues correspond to the formula

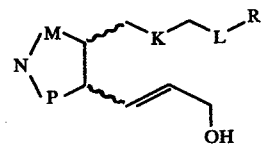

wherein:
L is methylene, ethylene or trimethylene;
K is ethylene or cis-vinylene;
M is carbonyl, α-hydroxymethylene, or β-hydroxymethylene;
N is methylene or methine, provided that N is methine only if P is methine and M is carbonyl;
P is methylene, ethylene, α-hydroxymethylene or methine, provided that P is methine only if N is methine; and,
R is carboxyl; hydroxymethylene, alkoxycarbonyl, the alkyl portion of said alkoxycarbonyl being a lower alkyl, or a pharmacologically acceptable non-toxic carboxy salt.

The analogues are prepared by first converting a trans-1-iodo-3-alkoxy-1-propene to the corresponding lithio compound. This lithio compound then combines with the hexamethylphosphorous triamide complex of copper(I) pentyne to give an alkenylcopper species. Reacting this alkenylcopper compound with the appropriate 2-substituted-cyclopent-2-enone or 2-substituted-cyclohex-2-enone gives the desired depentyl prostaglandins.

2 Claims, No Drawings

DEPENTYL ANALOGUES OF $PGE_1$

This is a division of application Ser. No. 684,569, filed Feb. 9, 1977 now U.S. Pat. No. 4,065,493.

BACKGROUND OF THE INVENTION

1. Field of the Invention

Compounds of this invention are analogues of natural prostaglandins.

Natural prostaglandins are twenty-carbon atom alicyclic compounds related to prostanoic acid which has the following structure:

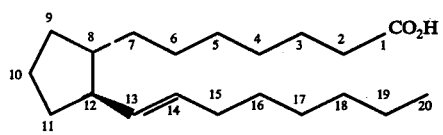
(I)

By convention, the carbon atoms of I are numbered sequentially from the carboxylic carbon atom. An important sterochemical feature of I is the trans-orientation of the sidechains $C_1$–$C_7$ and $C_{13}$–$C_{20}$. All natural prostaglandins have this orientation. In I, as elsewhere in this specification, a dashed line (-----) indicates projection of a covalent bond below a reference plane, such as those formed by the cyclopentyl ring or the bonds of a carbon atom (alpha-configuration), while a wedged line (▬) represents direction above that plane (beta-configuration). Those conventions apply to all compounds subsequently discussed in this specification.

In one system of nomenclature suggested by N. A. Nelson in J. Med Chem., 17: 911 (1972), prostaglandins are named as derivatives or modifications of the natural prostaglandins. In a second system, the I.U.P.A.C. (International Union of Pure and Applied Chemistry) system of nomenclature, prostaglandins are named as substituted heptanoic acids. A third system of nomenclature (also described by Nelson), names all prostaglandins as derivatives or modifications of prostanoic acid (structure I) or prostane (the hydrocarbon equivalent of structure I). The latter system is used by Chemical Abstracts.

Natural prostaglandins have the general structure,

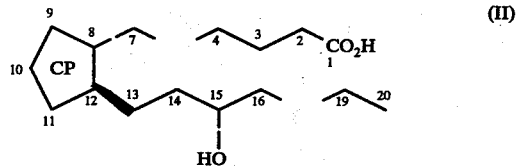
(II)

in which L and M may be ethylene or cis-vinylene radicals five-membered ring

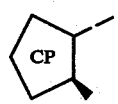

may be:

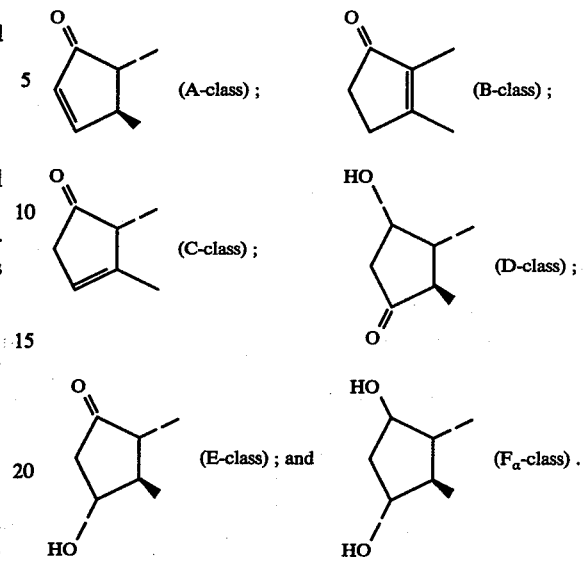

Prostaglandins are classified according to the functional groups present in the five-membered ring and the presence of double bonds in the ring or chains. Prostaglandins of the A-class (PGA or prostaglandin A) are characterized by an oxo group at $C_9$ and a double bond at $C_{10}$–$C_{11}$ ($\Delta^{10,11}$); those of the B-class (PGB) have an oxo group at $C_9$ and a double bond at $C_8$–$C_{12}$ ($\Delta^{8,12}$); compounds of the C-class (PGC) contain an oxo group at $C_9$ and a double bond at $C_{11}$–$C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the $F_\alpha$-class ($PGF_\alpha$) have an alpha-directed hydroxyl group at $C_9$ and an alpha-oriented hydroxyl group at $C_{11}$. Within each of the A, B, C, D, E, and F classes of prostaglandins are three subclassifications based upon the presence of double bonds in the side-chains at $C_5$–$C_6$, $C_{15}$–$C_{14}$, or $C_{17}$–$C_{18}$. The presence of a trans-unsaturated bond only at $C_{13}$–$C_{14}$ is indicated by the subscript numeral 1; thus, for example, $PGE_1$ (or prostaglandin $E_1$) denotes a prostaglandin of the E-type (oxo-group at $C_9$ and an alpha-hydroxyl at $C_{11}$) with a trans-double bond at $C_{13}$–$C_{14}$. The presence of both a trans-double bond at $C_{13}$–$C_{14}$ and a cis-double bond at $C_5$–$C_6$ is denoted by the subscript numeral 2; for example, $PGE_2$. Lastly, a trans-double bond at $C_{13}$–$C_{14}$, a cis-double bond at $C_5$–$C_6$ and a cis-double bond at $C_{17}$–$C_{18}$ is indicated by the subscript numeral 3; for example, $PGE_3$. The above notations apply to prostaglandins of the A, B, C, D, and F series as well; however, in the last, the alpha-orientation of the hydroxyl group at $C_9$ is indicated by the subscript Greek letter $\alpha$ after the numeral subscript.

The three systems of nomenclature as they apply to natural $PGE_{3\alpha}$ are shown below:

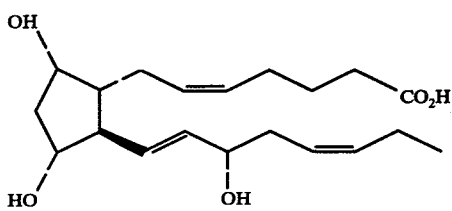

Nelson system: Prostaglandin $F_{3\alpha}$ or $PGF_{3\alpha}$ (shortened form);

I.U.P.A.C. system: 7-[3R,5S-Dihydroxy-2S-(3S-hydroxy-1E, 5Z-octadienyl)-cyclopent-1R-yl]-5Z-heptenoic acid; and, Chemical Abstracts system:- (5Z, 9$\alpha$,1-1$\alpha$,13E,15S,17Z)-9,11,15-trihydroxyprosta-5,13,17-trien-1-oic acid.

It is important to note that in all natural prostaglandins there is an alpha-oriented hydroxyl group at $C_{15}$. In the Cahn-Ingold Prelog system of defining stereochemistry, that $C_{15}$ hydroxyl group is in the S-configuration. The Cahn-Ingold-Prelog system is used to define stereochemistry of any asymmetric center outside of the carbocyclic ring in all three systems of nomenclature described above. This is in contrast to some prostaglandin literature in which the $\alpha,\beta$ designations are used, even at $C_{15}$.

Various derivatives and analogues of the prostaglandins described above may be synthesized. Although these derivatives do not occur as such in nature, many of them possess activity related to their parent compounds. Such synthetic derivatives and analogues include the following:

A. 11-Deoxy Derivatives of PGE and PGF Molecules

Formula II represents 11-deoxy PGE and PGF compounds when

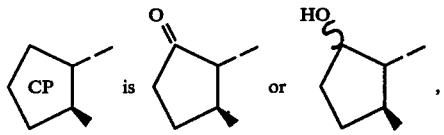

respectively. In that formula, and others of this patent specification, a swung dash or serpentine line (∼) denotes a covalent bond which can be either in the alpha-configuration (projecting below the appropriate reference plane) or in the beta-configuration (projecting above the reference plane).

B. $PGF_\beta$ Molecules

Formula II represents $PGF_\beta$ compounds when

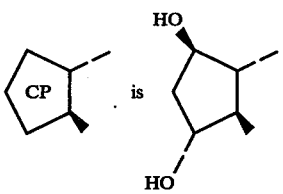

C. 9-Deoxy Derivatives of PGE

When

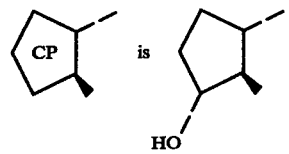

in Formula II, the formula gives the 9-deoxy derivatives of PGE.

D. 9-Deoxy-$\Delta^{9,10}$ Derivatives of PGE

Formula II represents the 9-deoxy-$\Delta^{9,10}$ PGE compounds when

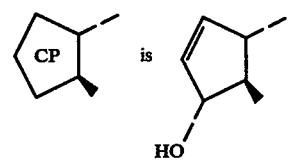

E. 9$\alpha$-Homo- and 9$\alpha$-Homo-11-Deoxy Derivative of PGE and PGF Molecules These compounds are given by Formula II when

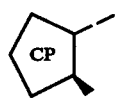

is replaced by

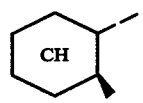

Specifically,

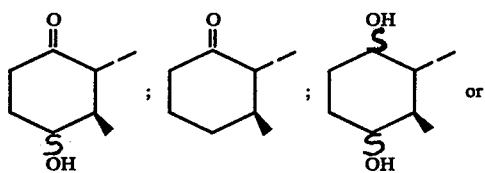

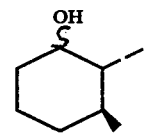

represent, respectively, the 9$\alpha$-homo-PGE, the 9$\alpha$-homo-11-deoxy-PGE, the 9$\alpha$-homo-PGF and the 9$\alpha$-homo-11-deoxy-PGF compounds.

F. 11α-Homo- Derivatives of PGE, PGF and PGA Molecules.

Replacement of

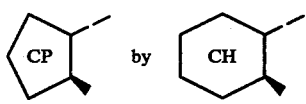

in formula II represents the continued molecules. In particular,

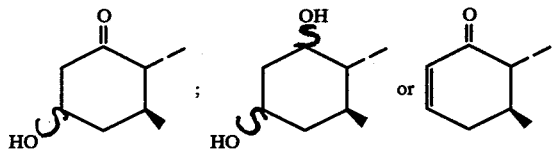

represent the 11α-homo-derivatives of, respectively, PGE, PGF and PGA.

G. 11-Epi-PGE and PGF Molecules

Formula II represents the 11-epi-compounds of PGE and PGF respectively, when

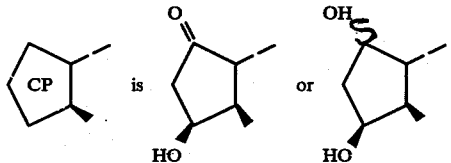

H. 8-Iso-, 12-Iso or 8,12-Bis-Iso-(Ent)-Prostaglandins

The 8-Iso-, 12-iso- or 8,12-bis-iso-(ent) compounds are obtained from Formula II by replacing:

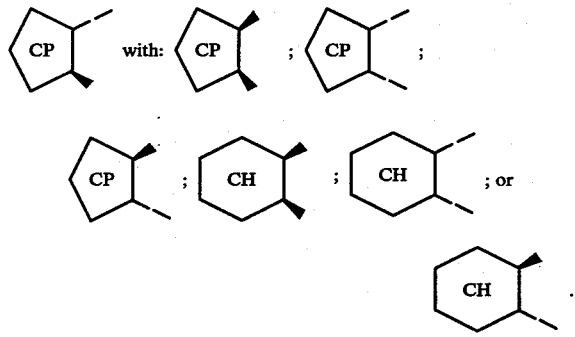

The iso modifications of Formula II may be divided into all of the sub-classes with varying ring oxygenation as described above.

Recent research indicates that prostaglandins appear ubiquitously in animal tissues. They, as well as many of their synthetic analogues, have important biochemical and physiological effects in a variety of mammalian systems.

In the endocrine system, for example, experimental evidence indicates prostaglandins influence the hormone synthesis or release of hormones in the secretory glands. In rats, $PGE_1$ and $PGE_2$ increase the release of the growth hormone while $PGA_1$ increases its synthesis. In sheep, $PGE_1$ and $PGF_{1\alpha}$ inhibit ovarian progesterone secretion. In a variety of mammals, $PGF_{1\alpha}$ and $PGF_{2\alpha}$ act as luteolytic factors. In mice, $PGE_1$, $PGE_2$, and $PGF_{1\alpha}$ and $PGF_{1\beta}$ increase thyroid activity. In hypophysectomized rats, $PGE_1$, $PGE_2$ and $PGF_{1\alpha}$ stimulate stereoidogenesis in the adrenal glands.

In the mammalian male reproductive system, $PGE_1$ contracts the smooth muscle of the vas deferens. In the female reproductive system, PGE and $PGF_\alpha$ compounds contract uterine smooth muscle. In general, PGE, PGB and PGA compounds relax in vitro human uterine muscle strips, while those of the $PGF_\alpha$ class contact such isolated preparations. PGE compounds, in general, promote fertility in the female reproductive system while $PGF_{2\alpha}$ has contragestational effects. $PGF_{2\alpha}$ also appears to be involved in the mechanism of menstruation. In general, $PGE_2$ produces potent oxytocic effects in inducing labor, while $PGF_{2\alpha}$ induces spontaneous abortions in early pregnancy.

$PGF_\alpha$ and PGE compounds have been isolated from a variety of nervous tissue and they seem to act as neurotransmitters. $PGE_1$ retards whereas $PGF_{2\alpha}$ facilitates transmission along motor pathways in the central nervous system. $PGE_1$ and $PGE_2$ reportedly inhibit transmitter release from adrenergic nerve endings in the guinea pig.

Prostaglandins stimulate contraction of gastrointestinal smooth muscle in vivo and in vitro. In dogs, $PGA_1$, $PGE_1$, and $PGE_2$ inhibit gastric secretion. $PGA_1$ exhibits similar activity in man.

In most mammalian respiratory tracts, PGE and PGF compounds affect in vitro preparations of tracheal smooth muscle. Specifically, $PGE_1$ and $PGE_2$ relax, while $PGF_{2\alpha}$ contracts, the smooth muscle. The human lung normally contains PGE and PGF compounds; consequently, some cases of bronchial asthma may involve an imbalance in the production or metabolism of those compounds.

Prostaglandins are involved in certain hematic mechanisms in mammals. $PGE_1$, for example, inhibits thrombogenesis in vitro through its effects on blood platelets.

In a variety of mammalian cardiovascular systems, compounds of the PGE and PGA classes are vasodilators whereas those of the $PGF_\alpha$ class are vasoconstrictors, by virtue of their action on vascular smooth muscle.

Prostaglandins naturally appear in the kidney and reverse experimental and clinical renoprival hypertension.

The prostaglandins and their analogues have broad clinical implications. In obstetrics and gynecology, they may find use in fertility control, treatment of menstrual disorders, the induction of labor, and the correction of hormone disorders. In gastroenterology, they may help treat peptic ulcers and various disorders involving motility, secretion, and absorption in the gastrointestinal tract. They may, in the respiratory area, prove beneficial in the therapy of bronchial asthma and other diseases involving bronchoconstriction. In hematology, they may display utility as anti-clotting agents in diseases such as venous thrombosis, thrombotic coronary occlusion and other diseases involving thrombi. For circulatory diseases, they have therapeutic utility in hypertension, peripheral vasopathies and cardiac disorders.

The following references include a more complete review of the chemical, physiological and pharmacological aspects of the prostaglandins: *The Prostaglan-* dins, Vol. I., P. Ramwell, Ed., New York, Plenum Press, 1973; Ann. N.Y. Acad. Sci., *180:* 1–568 (1971); Higgins and Braunwald, J. Am. Med. Assn., *53:* 92–112 (1972); Osterling, Marozowich, and Roseman, J. Phar. Sci., *61:* 1861–1895 (1972); and Nakano, Resident and Staff Phys., *19:* 92, 94–99, and 102–106 (1973).

SUMMARY OF THE INVENTION

Compounds of the formula

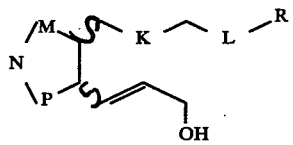
(III)

wherein:
- L is methylene, ethylene, or trimethylene;
- K is ethylene or cis-vinylene;
- M is carbonyl, α-hydroxymethylene, or β-hydroxymethylene;
- N is methylene or methine, provided that N is methine only if P is methine and M is carbonyl;
- P is methylene, ethylene, α-hydroxymethylene or methine, provided that P is methine only if N is methine; and
- R is carboxyl; hydroxymethylene, alkoxycarbonyl, the alkyl portion of said alkoxycarbonyl being a lower alkyl, or a pharmacologically acceptable non-toxic carboxy salt., although not possessing the C-16 to C-20 chain segment, nonetheless have, in various instances, displayed different types of biological activity.

Of the possible structures included within Formula III, those representing analogues of the A, E, and F prostaglandins constitute preferred subgeneric classes. Specifically, limiting L to ethylene, M to carbonyl, N and P to methine, and R to carboxyl, methoxycarbonyl, or ethoxycarbonyl gives the depentyl PGA analogues. With the appropriate stereochemistry of the side chains, they have the general structure:

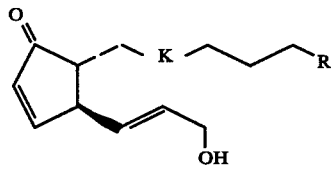
(IV)

With L, M, and R as above, but with N methylene and P α-hydroxymethylene, the structure of Formula III then becomes the depentyl analogues of the PGE compounds. These are encompassed by the general structure:

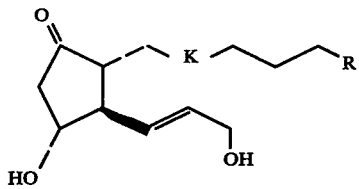
(V)

However, with P methylene rather than α-hydroxymethylene, compounds analogous to the 11-deoxy-derivatives of the E family result. The following general structure represents these compounds:

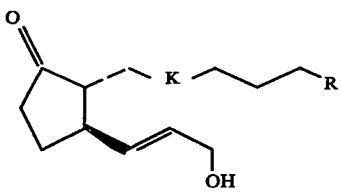
(VI)

Lastly, limiting L still to ethylene, N to methylene, M to α-hydroxymethylene or β-hydroxymethylene, P to α-hydroxymethylene gives the depentyl PGF$_\alpha$ or PGF$_\beta$ analogues, respectively. They have the generalized structure:

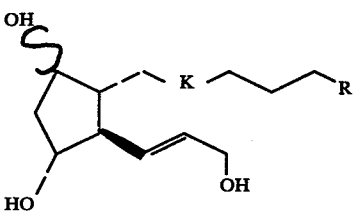
(VII)

Table I summarizes the reactions used to produce the depentyl analogues of the prostaglandins. In general, the method commences by mixing the trans-1-iodo-3-alkoxy-1-propene (VIII) with lithium metal or an alkyllithium compound. The reaction should proceed in a dry aprotic organic solvent under an inert atmosphere at a temperature of about −78° to 0° C. The aprotic solvent, of course, should not give off hydrogen, hydroxy, or ammonium radicals.

When using an alkyllithium (IXb) to substitute lithium for iodine in Formula VIII, the alkyl portion should have at lest two carbon atoms. It should also be a lower alkyl moiety, that is one with no more than four carbon atoms.

The R-group on the iodopropene (VIII) serves to protect the hydroxyl function as that molecule undergoes subsequent reaction. This, of course, requires the R-group to remain stable to the alkyllithium and alkylcopper compounds that it will encounter.

On the other hand, after the completion of the desired reactions, a mild acid treatment should suffice to remove the R-group and restore the hydroxyl function. The mild acid employed should generally not affect the structure of the molecule produced except to remove the hydroxyl-protecting group. Most carboxylic acids, and, in particular, oxalic, formic, or acetic acids, fall into this category. The tetrahydropyran-2-yl and 1-ethoxyethyl radicals have shown themselves as very suitable hydroxyl-protecting groups.

The lithiopropene (X) produced by the above reaction may then combine with the hexamethylphosphorus triamide complex of copper (I) pentyne (XI) to produce the mixed cuprate reactant (XII).

TABLE I:
Reactions for Producing the Depentyl Prostaglandin Analogues

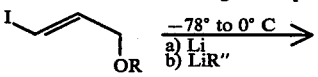

(VIII)    (IX)

-continued
TABLE I:
Reactions for Producing the Depentyl Prostaglandin Analogues

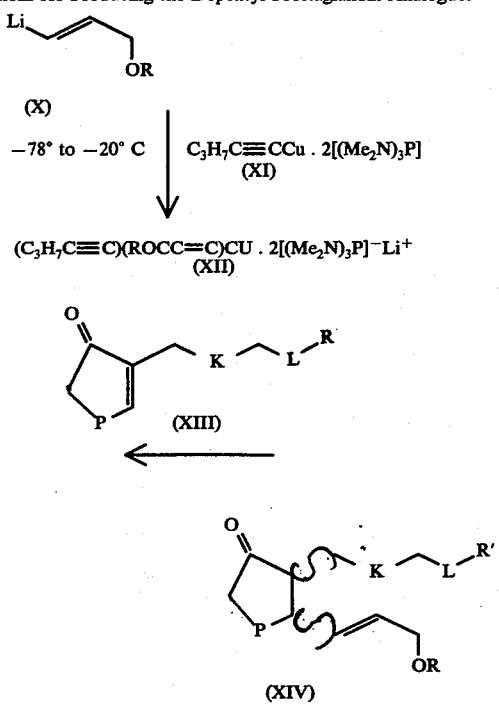

This reaction takes place readily in a dry aprotic solvent at a temperature of about −78° to −20° C.

The copper reagent thus produced may then react, also in a dry aprotic solvent, with the 2-substituted-cyclopent-2-enone (XIII). The general reaction involved has received discussion in Corey and Beames, J. Am. Chem. Soc., *94:* 7210–7211 (1972); Sih, Price, Sood, Salomon, Peruzzotti, and Casey, J. Am. Chem. Soc., *94:* 3643–3644 (1972); Sih, Solomon Price, Sood, and Peruzzotti, J. Am. Chem. Soc., *97:* 857–865 (1975); and Sih, Heather, Sood, Price, Peruzzotti, Lee and Lee, J. Am. Chem. Soc., *97:* 865–974 (1975).

In Formula XIII, K and L have the same meaning as that given for the final prostaglandins above. P may be methylene, ethylene, α-OR" or β-OR", where R" is also a hydroxyl-protecting group having the same properties as stated above for R. R' in structure XIII may be a loweralkyl alkoxycarbonyl, OR''', again, R''' represents a hydroxyl-protecting group with the same properties as R and R", above.

The reaction to attach the C-13 to C-15 segment of the depentyl prostaglandin, above, commences at a temperature of about −78° to −20° C. It then proceeds to completion at a temperature of about −20° to +25° C.

The above reactions normally produce a depentyl analogue of the E class of prostaglandins. These may then undergo subsequent reaction to produce the analogues of the A and F classes, as illustrated in Table II, and discussed in Pike, Lincoln, and Schneider, J. Org. Chem., *11:* 3552–3557 (1969).

Specifically to formulate the analogue of $PGA_1$, which bears the name of Methyl 15-hydroxy-9-oxo-16,17,18,19,20-pentanorprosta-10,13E-dien-1-oate (XVI), the depentyl $PGE_1$ (Methyl 11α,15-Dihydroxy-9-oxo-16,17,18,19,20-pentanorprost-13E-en-1-oate (XV) is mixed with a mild carboxylic acid at a relatively high temperature of about 50° to 70° C. Using acetic acid also gives the 15-acetate (XVII). On the other hand, mixing the same depentyl analogue of $PGE_1$ with sodium borohydride in a dry alcohol at about −20° to +25° C. will

TABLE II:
Producing the $PGA_1$ and $PGF_{1\alpha}$ and $PGF_{1\beta}$ Depentyl Analogues from the $PGE_1$ Analogue

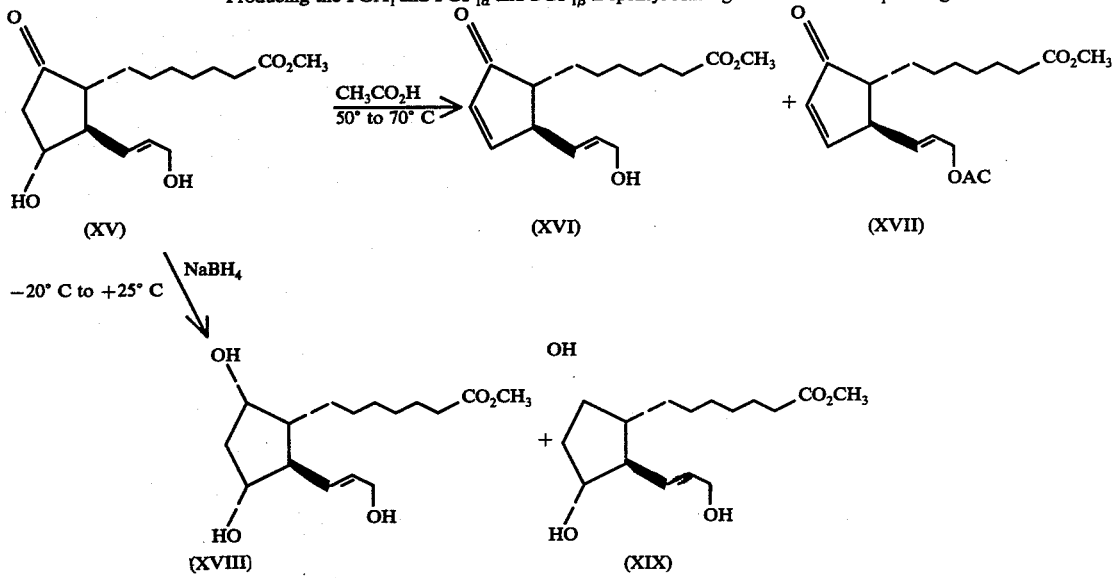

produce the depentyl analogues of $PGF_{1\alpha}$ (XVIII) and $PGF_{1\beta}$ (XIX).

DETAILED DESCRIPTION

Preparing the depentyl prostaglandin analogues according to the above reactions requires various initial reactants. These include the trans-1-iodo-3-hydroxy-1-propene (VIII) with a group protecting the hydroxy function, the hexamethylphosphorus triamide complex of copper(I) pentyne (XI) and the 2-substituted-cyclopent-2-enone (XIV). The last, where required, will also include a protected α-hydroxyl group on the cyclopentenone portion.

The copper reagent (XI) prepares most easily. It results simply from the mixing together of 0.407 g (3.12 mmol) of copper(I)pentyne, prepared according to the teaching of C. E. Castro et al., J. Org. Chem., *31:* 4071 (1966), with 1.15 ml of hexamethylphosphorus triamide (from the Aldrich Chemical Co., Inc.) dissolved in 8 ml of dry ether. Stirring the solution together for about 15 minutes at about 25° C will produce the copper reactant.

Trans-1-iodo-3-protected hydroxy-1-propene (VIII).

Various protecting groups can adequately protect the hydroxyl function at the C-3 site of the iodopropene. As discussed above, it must perform this protecting function during the reactions required to produce the prostaglandin analogue; it should also undergo facile removal with a mild acid treatment. While the following preparation involves the use of the 1-ethoxyethoxy group, Formula XX, the tetrahydropyran-2-yl moiety would proceed in a similar fashion.

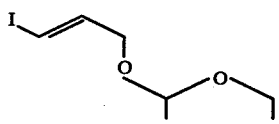
(XX)

Specifically, a mixture of 5.82 ml (100 mmol) of propargyl alcohol (obtained from the Aldrich Chemical Co., Inc.) and 80 ml of dry heptane was stirred under argon with ice-bath cooling as 25 ml (121 mmol) of triisobutylaluminum (from the Ethyl Corp.) was added dropwise at a rate such that the internal temperature of the reaction mixture never went above 10° C. A 22 ml (123 mmol) portion of diisobutylaluminum hydride (also from the Ethyl Corp.) was then added, and the resultant solution heated to 50° to 60° C for 3 hours. Distillation at 20 mm-Hg. removed the solvent with the vacuum released with argon. The residue was cooled to 0° C and then slowly diluted with 100 ml of dry tetrahydrofuran. The resultant solution was stirred at −78° C under argon as a solution of 62 g of iodine in 120 ml of dry tetrahydrofuran was added dropwise.

After coming to room temperature, the dark solution was quenched by the slow dropwise addition of 150 ml of 20% surfuric acid. An ice-bath maintained the reaction mixture at about 20° to 30° C. The resultant mixture was diluted with 250 ml of water and extracted with 4 portions of 250 ml of ethyl acetate.

The combined extracts were washed successively with saturated aqueous sodium bicarbonate, aqueous sodium thiosulfate and saturated aqueous sodium bicarbonate again. After the solution dried (Na$_2$SO$_4$), evaporating the solvent in vacuo gave a dark oil. This oil was dissolved in 25 ml of dry triethylamine and heated under argon at 85° to 95° C for 23 hours. The excess triethylamine was removed by evaporation in vacuo. The residue was partitioned between ethyl acetate and 10% HCl. The aqueous phase was extracted three more times with ethyl acetate. The combined extracts were washed with brine, dried (MgSO$_4$) and evaporated in vacuo to yield 7.3 g of a dark oil. Distilling this crude product in vacuo gave 4.2 g (22.8%) of pure trans-1-iodo-3-hydroxy-1-propene, which had the following physical chemical data:

Boiling point: 115° to 120° C (20 mm-Hg);

NMR(CDCl$_3$): δ 3.1 (1H, broad s), 4.07 (2H, d, J = 4.5 Hz), 6.34 (1H, d, J = 15 Hz), and 6.73 ppm (1H, d of t, J = 15, 4.5 Hz);

IR (film): 920, 960, 1005, 1070, 1170, 1235, 1610, 2860, 2925 and 3100 to 3600cm$^{-1}$ (broad).

A general description of this preparation has appeared in SiH, Heather, Peruzzotti, Price, Sood and Lee, J. Am. Chem. Soc., *95:* 1676-1677 (1973).

To protect the hydroxyl function, one drop of phosphorousoxychloride as added to a solution of 2.1 g of trans-1-iodo-3-hydroxy-1-propene in 5 ml of ethylvinyl ether under argon. The resultant solution remained at room temperature under argon for 20 hour. It was then diluted with ether and washed with saturated aqueous sodium bicarbonate. The wash solution was back extracted with ether. The combined extracts were dried (Na$_2$SO$_4$) and evaporated in vacuo to yield 2.8 g of a yellow oil which was then distilled in vacuo to yield 2.7 g of pure trans-1- iodo-3-(1-ethoxyethoxy)-1-propane (XX). In another run the same distillation produced extensive decomposition. As this decomposition was thought to be acid catalyzed, the product was subsequently distilled from a trace of anhydrous potassium carbonate. This reactant, used in preparing the depentyl prostaglandin analogues displayed the following physical chemical data:

Boiling point: 115° to 120° C (20 mm-Hg);

NMR (CDCl$_3$): δ 1.2 (3H, t, J=6.5 Hz.); 1.3 (3H, 3, J=5.3 Hz), 3.6 (2H, d, J=5.3 Hz). 3.6 (2H, complex), 3.95 (2H, d J=4.5 hz9, 4.75 (1H, q, J=5.3 Hz), 6.17 (1H, d, J=14 Hz), and 6.75 ppm (1H, d of t, J=18.5 Hz);

IR (Film): 930, 1055, 1085, 1130, 1340, 1385, 1605, 2910, and 2980 cm$^{-1}$.

2-Substituted-cyclopent-2-enone and
2-Substituted-cyclohex-2-enone (XIII)

As Formula XIII suggests, this reactant will have a six-membered cyclohexanone ring when P in the formula stands for ethylene. A five-membered cyclopentanone ring results otherwise.

For the analogues of the prostaglandins of the A$_1$, E$_1$, or F$_1$ classes, K in Formula XIII will again represent ethylene. For the E$_2$, A$_2$, and F$_2$ classes, K will stand for cis-vinylene.

Typically, the C-2 site in the cyclopentanone portion of Formula XIII has a seven-membered chain attached to it. In that case, L in Formula XIII stands for ethylene. Alternatively, the side chain may have six or eight conjoined carbon atoms when L represents methylene or trimethylene, respectively. The preparation of the reactants with these different chain lengths proceeds in a similar fashion as the seven-membered side chain. Clearly, however, the starting linear molecule which attaches to the cyclopentenone ring will have one fewer or more carbon atom, as appropriate.

The specific reactants used in preparing the exemplary depentyl prostaglandins below include 2-(6-carbomethoxyhexyl)-cyclopent-2-enone, 2-(6-carbomethoxy-cis-2-hexenyl)-cyclopent-2-enone, 2-(6-carbomethoxyhexyl)-4α-(tetrahydropyran-2-yloxy)-cyclopent-2-enone, and 2-(6-carbomethoxy-cis-2-hexenyl)-4α-(tetrahydropyran-2-yloxy)-cyclopent-2-enone. These represent compounds whose preparation the literature describes fairly well. The preparation of the first compound appears in the two articles: Sih, Solomon, Price, Sood and Peruzzotti, Tetrahedron Let., *24:* 2455-2437 (1972) and Sih et al., J. Am. Chem. Soc., *97:* 857-865 (1975). Grieco and Reap in J. Org. Chem., *38:*

3413–3415 (1973) detail the production of the second reactant above.

The preparation of the third utilized the compound 2-(6-carbomethoxyhexyl)-4α-hydroxy-2-cyclopent-2-enone, the origin of which has a discussion in Sih et al., J. Am. Chem. Soc., 95: 1676–1677 (1973). The hydroxyl group on this compound, of course, remains susceptible to attack in the reactions it undergoes. The article by Sih et al., J. Am. Chem. Soc., 97: 857–865 (1975), in the first column of page 862, describes how to protect the hydroxyl group through the addition of the tetrahydropyran-2-yl group. In fact, the article protects the hydroxyl group in the ethyl ester of the reactant, as opposed to the methyl ester as used here.

The preparation of the last compound above follows the synthetic route described in Heather, Sood, Price, Peruzzotti, Lee, Lee and Sih, Tetrahedron Let., 25: 2313–2316 (1973).

EXAMPLES

EXAMPLE 1 dl-11-Deoxy-15-depentyl-PGE$_1$
[(±)15-Hydroxy-9oxo-16,17,18,19,20-pentanorprost-13E-en-1-oic acid] (XXI).

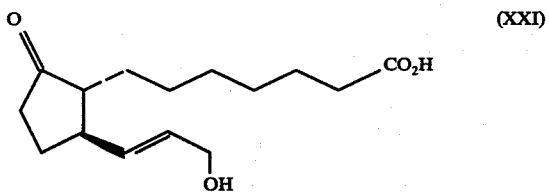

(XXI)

A solution of 0.798 g (3.12 mmol) of trans-1-ioxo-3-(1-ethoxyethoxy)-1-propen (XX) in 8 ml of dry ether was stirred at −78° C under argon as 3.67 ml (6.24 mmol) of a solution of t-butyllithium (1.7M) in pentane was added via syringe. The resultant solution was stirred for 2 hours at −78° C. It then received, via syringe, a solution of 0.407 g (3.12 mmol) of copper(I) pentyne solubilized with 1.15 ml of hexamethylphosphoroustriamide in 8 ml of dry ether. The resultant alkylcopper solution was stirred for 2 hours at −78° C.

A solution of 0.705 g (3.15 mmol) of 2-(6-carbomethexyl)-cyclopent-2-enone in 5 ml of dry ether was then added dropwise to the alkylcopper solution. The resultant mixture was stirred for 15 minutes at −78° C, then 1 hour at −20° C to −25° C, and then for 15 minutes at 0° C. The addition of 5 ml of 20% aqueous ammonium sulfate at 0° C quenched the reaction.

After diluting the resultant mixture with ether, 50 ml of cold 2% sulfuric acid was added. The resultant mixture was stirred vigorously and then filtered through diatomaceous earth (sold under the trademark Celite ® by the Johns Manvill Products Company). The filter pad received a thorough rinsing with ether. The organic layer of the filtrate was mixed with another portion of cold 2% sulfuric acid and then filtered again. The process was repeated until no additional solid appeared upon the addition of 2% sulfuric acid.

The combined aqueous wash layers were back extracted with ether several times. The combined extracts were washed with brine and saturated aqueous sodium bicarbonate. They were then dried (MgSO$_4$) and evaporated in vacuo. After dissolving in 20 ml of acetic acid-water-tetrahydrofuran (65:35:10), the resultant yellow oil remained under argon for 16 hours. Evaporation in vacuo removed the solvent, and ether dissolved the residue. The solution was washed twice with saturated aqueous sodium bicarbonate, and the wash solution twice back extracted with ether. The combined extracts were dried (MgSO$_4$) and evaporated in vacuo to give 0.7 g of crude dl-2α-(6-carbomethoxyhexyl)-3β-(3-hydroxy-1-trans-propenyl)-cyclopentanone as a yellow oil.

This oil dissolved in 10 ml of 5% potassium hydroxide in methanol-water (3:1) and remained at room temperature under argon for 3 hours. Again, the solvent was removed by evaporation in vacuo, and the residue dissolved in water and extracted with ethyl acetate. The extract was washed with water, and then was discarded. The combined aqueous phases were acidified with 10% hydrochloric acid and extracted several times with ethyl acetate. These combined extracts were dried (MgSO$_4$) and evaporated in vacuo. The yield was 0.742 g of crude dl-deoxy-15-depentyl PGE$_1$ (XXI) as a yellow oil. This crude product was purified by chromatography on silicic acid-Celite ® (80:20) using benzene-ethyl acetate gradient elution to give 208.4 mgm (24.9%) of pure XXI as a faint yellow oil. This compound displayed the following physical data:

NMR CDCl$_3$): δ 0.8–3.0 (18H, m), 4.2 (2H, broad d, J=3.5 Hz), 5.7 (2H, m) and 7.55 ppm (2H, broad s);

IR (film): 970, 1160, 1405, 1700–1740 (broad) 2860, 2930, and 2400–3600 cm$^{-1}$ (broad);

Mass Spectrum (70 eV): m/e 268(p), 250 (p-H$_2$O), 232 (p-2H$_2$O), 219, 193, 140, 122, 109 and others below 100.

EXAMPLE 2 dl-11-Deoxy-15-depentyl-PGE$_2$-Methyl ester [(±) Methyl 15-Hydroxy-9-oxo-16,17,18,19,20-pentanorprosta-5Z,13E-dien-1-oate] (XXII)

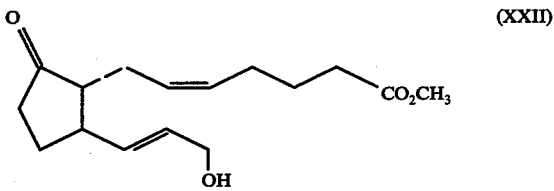

(XXII)

A solution of 0.773 g (3.02 mmol) of trans-1-iodo-3-(1-ethoxyethoxy)-1-propen (XX) in 3 ml of dry ether was stirred at −78° C under argon as a syringe added 3.55 ml (6.04 mmol) of a solution of t-butyllithium (1.7M) in pentane. The resultant solution was stirred for 2.3 hours at −78° C. To this first solution was then added dropwise a solution of 398 mgm (3.05 mmol) of copper(I)pentyne solubilized in 8 ml of ether with 1.15 ml of hexamethylphosphoroustriamide. The resultant mixture was stirred for 2.5 hour at −78° C before a solution of 677 mg (3.05 mmol) of 2-(6-carbomethoxy-cis-2-hexenyl)-cyclopent-2-enone in 8 ml of ether was added dropwise.

After warming to −20° C to −25° C, the resultant mixture was stirred for 2 hours. The dropwise addition of several ml of 20% aqueous ammonium sulfate then quenched it. The resultant mixture was diluted with ether and then stirred in an ice bath as 100 ml of 2% aqueous sulfuric acid was added slowly.

The resultant mixture was filtered through Celite ®. The filter pad was rinsed well with ether. The filtrate phases were separated, and the aqueous phase back extracted twice with ether. The combined extract was washed with brine and then saturated aqueous sodium bicarbonate. It was dried (MgSO₄) and evaporated in vacuo.

After dissolving in 25 ml of acetic acid-water-tetrahydrofuran (65:35:10), the resultant oily residue remained at room temperature overnight. Evaporation in vacuo removed the solvent and the residue was dissolved in ethyl acetate and washed with saturated aqueous sodium bicarbonate. Ethyl acetate twice back extracted the wash solution. The combined extract was dried (MgSO₄) and evaporated in vacuo to yield 0.791 g of crude (XXII). Purification by column chromatography on silicic acid-Celite® (85:15) using benzene-ethyl acetate gradient elution gave 278 mgm of pure (XXII). It had the following physical properties:

NMR (CDCl$_3$): δ 0.8–3.0 (14H, complex), 3.73 (3H, s), 4.2 (2H, broad d, J=3.5 Hz), 5.5 (2H, M), and 5.78 ppm (2H, m);

IR (film): 975, 1040, 1060, 1440, 1635, 2875, 2590 and 3100–3700 cm$^{-1}$(broad).

EXAMPLE 3

15-Depentyl-PGE$_1$ Methyl ester [Methyl 11α,15-Dihydroxy-9-oxo-16,17,18,19,20-pentanorprost-13E-en-1-oate] (XV)

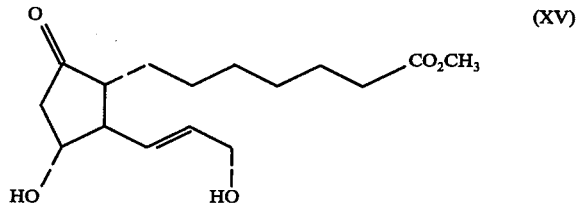

(XV)

A solution of 2.45 g (9.57 mmol) of trans-1-iodo-3-(1-ethoxyethoxy)-1-propene in 25 ml of dry ether was stirred under argon at −78° C as 11.3 ml (19.2 mmol) of a solution of t-butyllithium (1.7 M) in pentane was added dropwise. The resultant mixture was stirred for 2 hours at −78° C. Another solution was prepared by stirring 1.037 g (10.0 mmol) of copper(I)pentyne in 20 ml of ether with 3.67 ml of hexamethylphosphorous triamide until homogeneous.

This solubilized copper(I)pentyne solution was then added dropwise to the above alkenllithium solution with stirring at −78° C. The resultant mixture was stirred at −78° C for an additional 2 hours.

A third solution of 3.22 g (9.91 mmol) of 2-(6-carbomethoxyhexyl)-4α-tetrahydropyran-2-yloxy)-cyclopent-2-enone in 20 ml of ether was added dropwise with vigorous stirring to the above mixture. The resultant slurry then incurred stirring for 0.5 hour at −78° C and then at −23° C for 2 hours. The addition of 5 ml of 20% aqueous ammonium chloride at −20° C then quenched it.

The resultant mixture received dilution with ether and then stirring in an ice bath during the slow addition of 2% sulfuric acid. The resultant mixture was filtered through Celite® and the filter pad rinsed several times with ether. After the separation of the filtrate's phases, a further portion of 2% sulfuric acid washed the organic phase. Filtering the mixture again through Celite® removed precipitated copper(I)pentyne.

The resultant phases were separated and the aqueous phase back extracted several times with ether. The combined ether extracts were washed with brine and then saturated aqueous sodium bicarbonate. They were dried (MgSO₄) and then evaporated in vacuo to yield 4.4 g of a yellow oil.

This oil, after dissolving in 45 ml of acetic acid-water-tetrahydrofuran (65:35:10), remained for 20 hours at room temperature under argon. Evaporation in vacuo removed the solvent, and the residue was dissolved in ethyl acetate and washed with saturated aqueous sodium bicarbonate twice. The combined wash solution was back extracted three times with ethyl acetate. The combined extract was dried (MgSO₄) and evaporated in vacuo to yield 3.65 g of crude 15-depentyl-PGE$_1$-methyl ester (XV). Column chromatography on silicic acid-Celite® (85:15) using benzene-ethyl acetate gradient elution purified the residue to yield 870.6 mg of pure (XV) as a waxy faint yellow solid with the following properties:

NMR (CDCl$_3$): δ 0.8–3.0 (16H, complex), 3.6 (3H, s), 4.1 (5H, broad s) and 5.77 ppm (2H, m);

IR (film): 965, 1073, 1155, 1205, 1440, 1738, 2860, 2930, and 2930–3700 cm$^{-1}$(broad);

Mass Spectrum (70 eV): m/e 280 (p-H$_2$O), 262 (p-H$_2$O), 248 (p-H$_2$O)-CH$_3$OH), 236, 321, 204, 194, 177, 149, 138, 120, 107, and others below 100.

EXAMPLE 4

15-Depentyl-PGE$_2$-Methyl ester [Methyl 11α,15-Dihydroxy-9-oxo-16,17,18,19,20-pentanorprosta-5Z,13E-dien-1-oate] (XXIII)

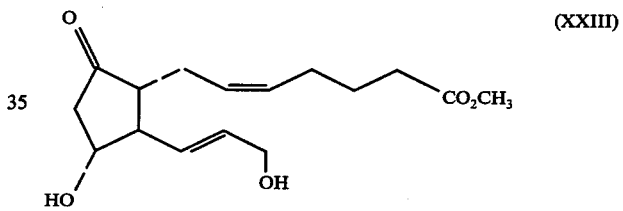

(XXIII)

A solution of 384 mgm (1.50 mmol) of trans-1-iodo-3-(1-ethoxyethoxy)-1-propene in 4 ml of dry ether was stirred at −78° C under argon during the dropwise addition of 2.0 ml (3.56 mmol) of a solution of t-butyllithium in pentane (1.8M) The resultant mixture underwent stirring at −78° C for 2 hours. A slurry of 197 mg (1.51 mmol) of copper(I)pentyne in 4 ml of dry ether was stirred with 0.55 ml of hexamethylphosphorous triamide under argon until homogeneous and then transferred dropwise via syringe to the above alkenyllithium solution. The resultant yellow solution was stirred for 1 hour at −78° C.

A third solution of 437 mgm (1.36 mmol) of 2-(6-carbomethoxy-cis-2-hexenyl)-4α-(tetrahydropyran-2-yloxy)-cyclopent-2-enone in 4 ml of dry ether was added dropwise to the above yellow solution. The resultant slurry received a brief stirring at −78° C, then at −15° to −20° C for 1.5 hours, and then at 0° C for 0.5 hour. The addition of several milliliters of 20% aqueous ammonium sulfate solution at 0° C quenched the reaction.

The resultant mixture was diluted with ether and then stirred in an ice bath through the addition of 50 ml of 2% aqueous sulfuric acid. The resultant mixture was stirred vigorously and then filtered through Celite®. The filter pad was washed several times with ether, the phases separated, and the aqueous phase back extracted twice with ether. The combined extract was washed with brine and saturated aqueous sodium bicarbonate, dried (MgSO$_4$) and evaporated in vacuo. Twenty-five ml of acetic acid-water-tetrahydrofuran (65:35:10) dissolved the residue which then remained under argon at room temperature for 20 hours. Evaporation in vauco removed the solvent, and ethyl acetate dissolved the residue. Saturated aqueous sodium bicarbonate washed the solution and the wash liquid was back extracted twice with ethyl acetate. The combined extract underwent drying (MgSO$_4$) and evaporation in vacuo. Chromatography on silicic acid-Celite ® (85:15) using benzene-ethyl acetate gradient elution purified the 0.446 g of resulting mixture residue to yield 76.5 mgm of the 15-depentyl-PGE$_2$-methyl ester (XXIII) as a faintly yellow oil. The compound had the following characteristics:

NMR (CDCl$_3$): δ 1.0–3.0 (12H, complex), 3.6 (2H, broad s), 3.65 (3H, s), 4.15 (3H, m), 5.4 (2H, broad s), and 5.75 ppm (2H, m);

IR (film): 975, 998, 1082, 1160, 1250, 1440, 1740, 2850, 2940, and 3100–3700 cm$^{-1}$ (broad s).

EXAMPLE 5

15-Depentyl-PGA$_1$-Methyl ester [Methyl 15-Hydroxy-9-oxo-16,17,18,19,20-pentanorprosta-10,13E-dien-1-oate] (XIV) and 15-Depentyl-PGA$_1$-Methyl ester-15-Acetate [Methyl 15-Acetoxy-9-oxo-16,17,18,19,20-pentanorprosta-10,13E-dien-1-oate] (XVII)

A solution of 149 mgm of 15-depentyl-PGE$_1$-methyl ester, prepared as in Example 3, in 4.5 ml of acetic acid and 0.5 ml of water was stirred at 60° C under argon for 16 hours. The resultant yellow solution was evaporated in vacuo. The residue was dissolved in ether and washed with saturated aqueous sodium bicarbonate. Ether twice back extracted the wash solution. Drying (MgSO$_4$) and evaporating the combined extracts in vacuo yielded 142 mgm of an orange oil. Purifying the residue by preparative thin layer chromatography on a 20 × 20 cm × 2 mm silic gel PF254 plate by eluting with ether gave two major U.V.-active bands which ether then washed from the silica.

The yield of 76.3 mgm of the 15-depentyl-PGA$_1$-methyl ester (XVI) had the following physical data:

NMR (CDCl$_3$): δ 0.8–2.5 (14H, m), 3.3 (1H, m), 3.68 (3H, s), 4.13 (2H, d, J=3.5 Hz), 5.7 (2H, m), 6.18 (1H, m) and 7.5 ppm (1H, m);

IR (film): 800, 974, 1010, 1095, 1180, 1200, 1350, 1440, 1590, 1710, 1740, 2860, 2940, and 3100–3700 cm$^{-1}$ (broad).

Mass Spectrum (70 eV): m/e 280 (p), 262 (p-H$_2$O), 248 (p-CH$_3$OH), 231 (p-H$_2$O—CH$_3$OH), 138, 133, 120, 107, and others below 100.

The second major band (higher R$_f$) produced 24.0 mgm of 15-depentyl-PGA$_1$-methyl ester-15-acetate (XVII), which displayed the following characteristics:

NMR (CDCl$_3$): δ 0.8–2.5 (14H, m), 2.07 (3H, s), 3.3 (1H, m), 3.68 (3H, s), 4.52 (2H, m), 5.7 (2H, m), 6.15 (1H, m) and 7.5 ppm (1H, m).

IR (film): 800, 974, 1010, 1095, 1130, 1200, 1350, 1440, 1590, 1710, 1740, 2860, and 2940 cm$^{-1}$.

EXAMPLES 6 and 7

15-Depentyl-PGF$_{1\alpha}$-Methyl ester [Methyl 16,17,18,19,20-Pentanor-9α,11α,15-trihydroxyprost-13E-en-1-oate] (XVIII) and 15-Depentyl-PGF$_{1\beta}$-Methyl ester [Methyl 16,17,18,19,20-Pentanor-9β,11α,15-trihydroxyprost-13E-en-1-oate] (XIX)

A solution of 482 mgm of 15-depentyl-PGE$_1$-methyl ester (XV), prepared as in Example 3, in 25 ml of dry methanol was stirred at 0° C during the addition, over 10 minutes, of a total of 1.01 g of sodium borohydride in several portions. The resultant solution was stirred for 1 hour at 0° C and then 1 hour at room temperature. Evaporation in vacuo removed the solvent. The white residue was partitioned between ethyl acetate and brine. After separating the phases, ethyl acetate extracted the aqueous layer three times. Drying (mgSO$_4$) and evaporating in vacuo yielded 420.8 mgm of a clear oil. Separating this residue into components by column chromatography on silicic acid-Celite ® (85:15) using benzene-ethyl acetate gradient elution gae 105.1 mgm of the less polar 15-depentyl-PGF$_{1\alpha}$-methyl ester (XVIII) (R$_f$0.13, tlc) and 141.2 mgm of the more polar 15-depentyl-PGF$_{1\beta}$-methyl ester (XIX) (R$_f$ 0.10, tlc). Also obtained was 7.5 mgm of a mixed fraction.

These thin-layer chromatography determinations used a solvent prepared by shaking thoroughly a mixture of 1100 ml of ethyl acetate, 200 ml of acetic acid, 500 ml of isooctane and 1000 ml of water and allowing them to settle for several hours. The lower phase is removed and discarded. The upper phase is used as the developing solvent. After developing with this solvent, the tlc plate is air dried with brief warming.

To allow visualization of the tlc results, a solution is prepared by diluting an 84 ml portion of concentrated sulfuric acid to 1 liter with deionized water. A 30 g portion of ceric sulfate is slowly stirred into the dilute acid. The tlc plate then receives a spray of this acid solution and a heating at 250° C for approximately 1 minute. The prostaglandins appear as brown spots on the plate as a result of the treatment.

The PGF$_{1\alpha}$ (XVIII) and PGF$_{1\beta}$ (XIX) depentyl analogues have the following identical spectra:

NMR (CDCl$_3$): δ 0.7–2.5 (16H, complex), 3.6 (3H, s), 4.17 (7H, broad m), and 5.65 ppm (2H, m).

IR (film): 965, 995, 1040, 1080, 1100, 1167, 1195, 1440, 1720, 1735, 2850, 2920, and 3100–3600 cm$^{-1}$ (broad).

Mass Spectrum (70 eV): m/e 282 (p-H$_2$O), 251 (p-H$_2$O—CH$_3$O), 246 (p-3H$_2$), 233, 210, 178, 150, 140, 136, 121, 107 and other below 100.

EXAMPLE 8

Biological Activity

The compounds from Example 1 through 7 above underwent a variety of tests to determine their biological activity. The resports below resulted from tests in which the compounds displayed the most consistent activity, as a group.

The other experiments undertaken, in general, produced less or no activity for most of the compounds. Some of these tests did produce some activity for one or more analogoues. This latter group of tests included the effects of the depentyl prostaglandin analogues on:

(a) the rat uterus in vitro;
(b) the guinea pig trachea in vitro;

(c) blood pressure and heart rate in the anesthetized cat;
(d) blood pressure in the hypertensive rat;
(e) gastric secretions in the rat; and
(f) the action of the natural prostaglandins on the guinea pig ileum in vitro.

EXAMPLE 8A

Cascade Assay

The smooth muscle stimulant effects of test compounds are determined simultaneously in four different tissues which are known to be contracted by naturally occurring prostaglandins. Segments of rat stomach fundus, rat colon, chick rectum and rabbit aortic strip are obtained as described by Vane, Brit. J. Pharmacol., 12: 344 (1957); Regoli and Vane, Brit. J. Pharmacol., 23: 351 (1964); Mann and West, Brit. J. Pharmacol., 5, 173 (1950); and Furchgott and Bhadrakom, J. Pharmacol. Exper. Ther., 108: 129 (1953).

One end of each preparation is tied to the bottom of a 10 ml tissue chamber and the other to a grass Ft-03 force displacement transducer for continuous tension recording. The stomach, colon and rectrum segments are stretched to an initial tension of 1 g, while the aortic strip is subjected to 4 g. All preparations remain undisturbed for 1 hour. The chambers possess an external jacket in which water at 40° C circulates to keep the tissues warm. Preparations are arranged one beneath the other, aorta, stomach, colon and rectum in descending order.

Provison is made for bathing the four tissues successively so that they are superfused (Gadum, Brit. J. Pharmacol., 6: 321 (1953) with the same fluid. This consists of Krebs bicarbonate solution bubbled with a mixture of 95% $O_2$ and 5% $CO_2$, warmed at 37° C and containing atropine sulphate (0.1 mcgm/ml), phenoxybenzamine hydrochloride (0.1 mcgm/ml), propranolol hydrochloride (3.0 mcgm/ml) methysergide maleate (0.2 mcgm/ml) and brompheniramine maleate (0.1 mcgm/ml), in order to eliminate the possibility of smooth muscle responses being due to stimulation of cholinergic, adrenergic, serotonin or histamine receptors. The fluid, circulated by means of a roller pump, drips over the preparations at a rate of 10 ml/minute.

Test compounds are diluted from stock solutions in order to administer quantities ranging from 0.001 to 100,000 ngm in a volume of 0.5 ml. The drugs are applied by dripping on the uppermost tissue, at intervals of 10 to 20 minutes. Maximal increases in tensio after each dose are measured and results used to plot dose-response curves. The results for the rat stomach fundus appear in Table III.

Table III

Results of Cascade Analysis for Rat Stomach Fundus - G Tension

| Depentyl Analogue Dose ngm. | $PGE_1$ | 11-Deoxy $PGE_1$ | $PGE_2$ | 11-Deoxy $PGE_2$ | $PGF_{1\alpha}$ | $PGF_{1\beta}$ |
|---|---|---|---|---|---|---|
| 0.001 | 0.5 | 0.4 | 0.1 | 0.3 | 0.5 | 0.4 |
| 0.01 | 0.5 | 0.4 | 0.3 | 0.3 | 0.4 | 0.5 |
| 0.1 | 0.4 | 0.4 | 0.3 | 0.3 | 0.6 | 0.6 |
| 1.0 | 0.5 | 0.4 | 0.3 | 0.6 | 0.5 | 0.4 |
| 10 | 0.5 | 0.5 | 0.3 | 0.5 | 0.5 | 0.4 |
| 100 | 0.5 | 0.5 | 0.3 | 1.0 | 0.5 | 0.5 |
| 1,000 | 3.2 | 0.5 | 0.3 | 0.7 | 0.5 | 0.4 |
| 10,000 | 4.2 | 0.5 | 0.6 | 2.2 | 0.5 | 0.4 |
| 100,000 | 5.8 | 2.6 | 1.0 | 3.2 | 0.5 | 0.3 |

EXAMPLE 8B

Gastric Secretion in the Rat

Utilizing the procedure of Lepman, J. Pharm. Pharmacol., 21: 355 (1968), rats of one sex weighing 150 to 200 g are randomly divided into groups of six animals each and fasted for the 48 hours previous to the experiments, water being available ad libitum. The animals are anesthetized with ether, the abdomen opened through a midline incision, and the pylorus ligated. Test compounds are diluted from stock solution in order to administer a dose of 1.5 mg/kg in a volume equivalent to 1 ml/kg. Subcutaneous injections are applied immediately after surgery and again 2 hours later to administer a total dose of 3.0 mg/kg.

Solutions with phosphate buffer, as recommended by Lee, Bianchi, Mollisan and Hansen, J. Prostaglandins, 3: 29 (1973), insure adequate stability of drugs at the subcutaneous depot. Each compound is tested in one group of rats; an additional control group receives only the vehicle.

Four hours after pyloric ligation, the animals are killed with ether, the cardias ligated and the stomachs removed. The volume of gastric secretion is measured and the contents centrifuges at 5000 rpm for 10 minutes. Total acid in the supernatant is titrated against a 0.1 N sodium hydroxide solution and the amount expressed in mEq. Volume and total acid values of the treated group are compared with those of the controls by the t test. The results appear in Table IV.

EXAMPLE 8C

Inhibition of Human Platelet Aggregation

The ability of test compounds to inhibit platlet aggregation was determined by a modification of the turbidometric technique of Born in Nature, 194: 927 (1962). Blood, collected from human volunteers who had not ingested aspirin or aspirin-containing products within the preceding two weeks in heparinized containers, was allowed to settle for one hour. The platelet rich plasma (PRP) supernates were collected and pooled. Siliconized glassware was used throughout.

In the assay, 1.9 ml of the PRP and 0.2 ml of the test compound at the appropriate concentration (0.001 to 100 mcgm), or 0.2 ml of distilled water as a control, were placed in sample cuvettes.

Table IV

Results for Gastric Secretion in the Rat

| Depentyl Analogue | Volume Change-% | Total Acid Change-% |
|---|---|---|
| $PGA_1$ | +19 | +22 |
| $PGE_1$ | −25 | −30 |
| 11-Deoxy $PGE_1$ | −36 to −10 | −57 to −14 |
| $PGE_2$ | −14 | −9 |
| 11-Deoxy | −24 | −35 |

Table IV-continued

| | Results for Gastric Secretion in the Rat | |
|---|---|---|
| Depentyl Analogue | Volume Change-% | Total Acid Change-% |
| $PGE_2$ | | |
| $PGF_{1\alpha}$ | −38 | −41 |
| $PGF_{1\beta}$ | +23* | +19* |

*Determinations made at six rather than four hours after surgery.

The cuvettes were placed in a 37° C incubation block for 15 minutes and then in a spectrophotometer linked to a strip chart recorder. After 30 to 60 seconds, 0.2 ml of a solution, prepared by diluting a calf skin collagen solution (from Worthington Biochemical) 1:9 with Tyrodes' Solution was added to each cuvette. A decrease in optical density evidenced platelet aggregation.

The calculation of the degree of inhibition of platelet aggregation exhibited by each concentration of test compound followed the method of Caprino, Borrelli, and Falchetti, Arzneim-Forsch, 23: 1277 (1973). The results appear in Table V.

Table V

| | Results of Inhibition of Human Platelet Aggregation-% | | | | |
|---|---|---|---|---|---|
| Depentyl Analogue Dose mcgm | $PGE_1$ | $PGE_2$ | 11-Deoxy | $PGF_{1\alpha}$ | $PGF_{1\beta}$ |
| 0.001 | 29 | 2 | 2 | 5 | 30 |
| 0.01 | 17 | 5 | 2 | 2 | 19 |
| 0.1 | 24 | 7 | −9 | 7 | 24 |
| 1.0 | 19 | −2 | 2 | 15 | 78 |
| 10 | 19 | 5 | −6 | 22 | 26 |
| 100 | 19 | 2 | −4 | 8 | 4 |

What is claimed is:

1. A compound of the formula,

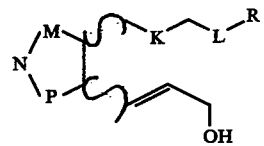

wherein:
L is methylene, ethylene, or trimethylene;
K is ethylene or;
M is carbonyl;
N is methylene;
P is α-hydroxymethylene; and
R is carboxyl; alkoxycarbonyl, the alkyl portion of said alkoxycarbonyl being a lower alkyl radical; or a pharmacologically acceptable non-toxic carboxyl salt.

2. The compound as in claim 1, 15-depentyl-$PGE_1$ methyl ester.

* * * * *

UNITED STATES PATENT AND TRADEMARK OFFICE
CERTIFICATE OF CORRECTION

PATENT NO. : 4,100,356     Page 1 of 2
DATED      : July 11, 1978
INVENTOR(S): Harold Clinton Kluender It is certified that error appears in the above-identified patent and that said Letters Patent are hereby corrected as shown below:

Title Sheet, Item [62], change "Feb. 9, 1977" to --May 10, 1976--.
Column 1, Line 4, change "Feb. 9, 1977" to --May 10, 1976--.

Column 1, Lines 51-58, delete the formula and substitute therefor,

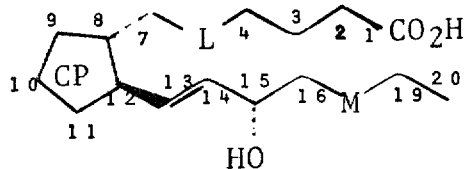

Column 6, Line 12, change "contact" to --contract--.

Column 8, Line 39, change "lest" to --least--.

Table II bridging Columns 9 and 10, delete Formula XIX and substitute therefor,

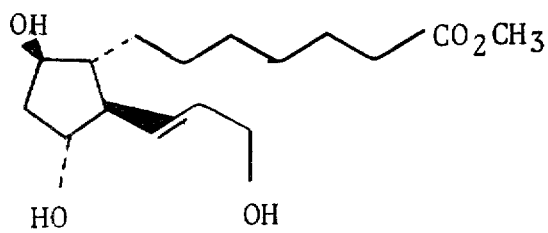

UNITED STATES PATENT AND TRADEMARK OFFICE
CERTIFICATE OF CORRECTION

PATENT NO. : 4,100,356

DATED : July 11, 1978

INVENTOR(S) : Harold Clinton Kluender

It is certified that error appears in the above-identified patent and that said Letters Patent are hereby corrected as shown below:

Column 12, Line 30, change "hz9" to --hz)--.

Column 12, Line 66, change "24:2455-2437" to --24:2435-2437--.

Column 18, Line 23, change "gae" to --gave--.

Column 19, Line 65, change "tensio" to --tension--.

Column 20, Line 38, change "centrifuges" to --centrifuged--.

Column 22, Line 26, delete the "semicolon (;)" and insert the word --or-- in its stead.

Signed and Sealed this

Twenty-second Day of May 1979

[SEAL]

Attest:

RUTH C. MASON
Attesting Officer

DONALD W. BANNER
Commissioner of Patents and Trademarks